United States Patent
Volker et al.

(10) Patent No.: US 10,295,458 B2
(45) Date of Patent: May 21, 2019

(54) ANALYTICAL DEVICE FOR DETERMINING A DIGESTION PARAMETER OF A LIQUID SAMPLE

(71) Applicant: Endress + Hauser Conducta Gesellschaft für Mess- und Regeltechnik mbH + Co. KG, Gerlingen (DE)

(72) Inventors: Marco Volker, Schwetzingen (DE); Sofia Reim, Gerlingen (DE); Anja Gerlinger, Stuttgart (DE); Xu Zhou, Ingersheim (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 14/562,814

(22) Filed: Dec. 8, 2014

(65) Prior Publication Data
US 2015/0168373 A1   Jun. 18, 2015

(30) Foreign Application Priority Data
Dec. 16, 2013   (DE) .................. 10 2013 114 138

(51) Int. Cl.
  *G01N 21/27*   (2006.01)
  *G01N 35/10*   (2006.01)
(52) U.S. Cl.
  CPC ......... *G01N 21/27* (2013.01); *G01N 35/1095* (2013.01); *G01N 2201/062* (2013.01)
(58) Field of Classification Search
  CPC . B01D 2252/103; B01D 53/1456; C02F 1/68; C02F 2101/12; G01N 1/38;
  (Continued)

(56) References Cited

U.S. PATENT DOCUMENTS 5,459,075 A    10/1995   Fabinski
5,817,954 A *  10/1998   Kahng ............... G01N 33/1886
                                                   422/75
(Continued)

FOREIGN PATENT DOCUMENTS

CN    1095992 C    12/1994
CN    1629623 A     6/2005
(Continued)

OTHER PUBLICATIONS

English machine translation for WO 2005064328 A1; published Jul. 14, 2005.*
(Continued)

*Primary Examiner* — Lyle Alexander
*Assistant Examiner* — Bryan Kilpatrick
(74) *Attorney, Agent, or Firm* — Christopher R. Powers; PatServe

(57) ABSTRACT

An analytical device for determining a parameter of a liquid sample, especially a digestion parameter, such as chemical oxygen demand, total carbon content or total nitrogen content, comprising a reactor, and measuring system for ascertaining the parameter of the liquid sample. A container system for storing samples, reagents and waste products in containers, a transport and dosing system for metering and transporting the sample and reagents from the containers into a metering container and for disposal of waste products from the metering container into a waste container, and a measuring transducer for registering a measured parameter correlating, measured value of the liquid sample mixed in the reactor, and measuring, system, in given cases, with one or more reagents is provided. The transport and dosing system is embodied at least of a metering container, a piston pump and an additional sample taking apparatus at least for
(Continued)

removal from a sample taking location of a predetermined volume of a liquid as a liquid sample.

12 Claims, 1 Drawing Sheet

(58) Field of Classification Search
CPC .... G01N 1/4044; G01N 33/1826; G01N 1/44; G01N 21/27; G01N 21/5907; G01N 2201/062; G01N 33/1806; G01N 35/1095
USPC ...................................... 422/68.1, 79, 82.05
See application file for complete search history.

(56) References Cited

U.S. PATENT DOCUMENTS

| | | | |
|---|---|---|---|
| 5,993,742 | A | 11/1999 | Binz |
| 8,236,567 | B2 | 8/2012 | Kathe |
| 9,435,729 | B2 * | 9/2016 | Bernhard ........... B01D 19/0036 |
| 2008/0220533 | A1 | 9/2008 | Fujiyama |
| 2012/0173164 | A1 * | 7/2012 | Steuerwald ............ G01N 35/08 702/25 |
| 2012/0285224 | A1 | 11/2012 | Zachmann |
| 2013/0149790 | A1 | 6/2013 | Mennicken |
| 2013/0156646 | A1 * | 6/2013 | Bernhard ........... B01D 19/0036 422/82.09 |
| 2015/0168366 | A1 * | 6/2015 | Volker ............... G01N 33/1806 422/79 |

FOREIGN PATENT DOCUMENTS

| | | | |
|---|---|---|---|
| CN | 101184993 | A | 5/2008 |
| CN | 101988900 | A | 3/2011 |
| CN | 102854054 | A | 1/2013 |
| DE | 19629835 | A1 | 1/1998 |
| DE | 10360066 | A1 | 7/2005 |
| DE | 102009028165 | A1 | 2/2011 |
| DE | 102009029305 | A1 | 3/2011 |
| DE | 102011075762 | A1 | 11/2012 |
| DE | 102011088235 | A1 | 6/2013 |
| DE | 102011088959 | A1 | 6/2013 |
| JP | 6265538 | A | 9/1994 |
| KR | 101307971 | | 4/2013 |
| WO | 9943621 | A1 | 9/1999 |
| WO | 2005064328 | A1 | 7/2005 |
| WO | WO 2005064328 | A1 * | 7/2005 ........... G01N 21/251 |

OTHER PUBLICATIONS

German Search Report, German Patent Office, Munich, dated Jan. 28, 2014.

Chinese Office Action, Chinese Patent Office, Beijing, China, dated Dec. 16, 2015 (English translation of office action attached).

* cited by examiner

ANALYTICAL DEVICE FOR DETERMINING A DIGESTION PARAMETER OF A LIQUID SAMPLE

TECHNICAL FIELD

The invention relates to an analytical device for determining a digestion parameter of a liquid sample.

BACKGROUND DISCUSSION

The determining of digestion parameters in liquid samples plays a role, for example, in process measurements technology or in industrial measurements technology, especially in the field of water and waste water treatment and/or in water and waste water analysis. Important examples of digestion parameters include chemical oxygen demand (COD), total carbon content and total nitrogen content ($N_{tot}$).

Chemical oxygen demand is the oxygen equivalent amount of a chemical compound, usually a strong oxidizing agent, which is consumed by the oxidizable constituents contained in a certain volume of a liquid sample under the reaction conditions of a prescribed method. Serving as oxidizing agent, in such case, is frequently potassium dichromate. The COD value is, besides the total nitrogen content, an important parameter for classifying the degree of pollution in the case of river water and in waste water and clarification plants, especially those containing organic impurities.

In known methods for determining such digestion parameters, first of all, the liquid sample is mixed with a digestion agent in a digestion container, most often as one embodied as a cuvette. This reaction mixture is heated, in given cases, under pressure, for a predetermined time in the digestion container. The substances to be detected, on whose concentration the given digestion parameter depends, are, in such case, dissolved by chemical reaction with the digestion agent. Depending on the type of digestion parameter to be detected, either the consumption of the digestion means or a reaction with one or more additional reagents added to the reaction mixture brings about a change in the chemical and/or physical properties, e.g. the extinction, respectively absorption, of the liquid sample. This change can be detected, for example, by means of a suitable electrochemical transducer or, e.g. in the case of a change of extinction, respectively absorption, by means of a photometric, measuring transducer. The current value of the digestion parameter can be ascertained based on a measurement signal provided by the measuring transducer.

In the case of most methods for determining chemical oxygen demand, for example, a sample is treated with a known excess of an oxidizing agent and then the consumption of the oxidizing agent ascertained, for example, through back titration of the not consumed remainder. Photometrically ascertaining the consumption of oxidizing agent represents another option, e.g. when potassium dichromate serves as the oxidizing agent. The amount of consumed oxidizing agent is converted into equivalent oxygen amount.

Known from the state of the art is a series of analytical devices for determining digestion parameters according to such methods. Described in German patent application DE 103 60 066 A1, for example, is an analytical device for photometrically determining the chemical oxygen demand of a liquid sample, wherein a reaction mixture in a cuvette of the liquid sample and potassium dichromate as oxidizing agent is heated under pressure-tight closure for a digestion time at a temperature above the atmospheric boiling temperature of the reaction mixture. At the same time, the extinction of the reaction mixture in the cuvette as the digestion progresses is determined at at least one fixed wavelength, wherein the change of the extinction serves as a measure for the concentration change and therewith for the consumption of the oxidizing agent.

Furthermore, described in International Published Application, WO 002005064328 A1 is a method for metering a liquid, wherein the liquid in a metering chamber with light barriers is dosed only by means of a piston pump. In the case of this embodiment of the dosing, metering and transport unit, the following problems occur. Due to the long hose length for sample taking in the sample container, only a limited sucking distance and sucking height is possible by means of this arrangement. The sample liquid can only be sucked in by a negative pressure supplied by the piston pump. If the volume to be sucked in is, due to the hose length of the sample liquid transport line, greater than the suction volume of the piston pump, predetermined volumes can be sucked in only by multiple actuations of the piston pump and therewith increasing the negative pressure only by multiple operation of the piston pump. This greatly increases the time consumed for pumping the liquid samples, since piston pumps move only relatively slowly, and, moreover, the piston pump experiences increased wear from the greater mechanical loading and the higher negative pressure.

SUMMARY OF THE INVENTION

It is, consequently, an object of the invention to provide a digestion reactor and an analytical device for determining a digestion parameter of a liquid sample using a dosing, metering and supply unit, which overcomes the described disadvantages.

The object is achieved by an analytical device for determining a parameter of a liquid sample.

The object is achieved by an analytical device for determining a parameter of a liquid sample, especially a digestion parameter, such as chemical oxygen demand, total carbon content or total nitrogen content, at least comprising:

- a reactor, and measuring, system for ascertaining the parameter of the liquid sample;
- a container system for storing samples, reagents and waste products in containers;
- a transport and dosing system for metering and transporting the sample and reagents from the containers into a metering container and for disposal of waste products from the metering container into a waste container; and
- a measuring transducer for registering a measured parameter correlating, measured value of the liquid sample mixed in the reactor, and measuring, system, in given cases, with one or more reagents, wherein:
- the transport and dosing system is embodied at least of a metering container, a piston pump and an additional sample taking apparatus at least for removal from a sample taking location of a predetermined volume of a liquid as a liquid sample.

In an additional embodiment, the sample taking apparatus is embodied as a peristaltic pump. Thus, instead of the piston pump, a peristaltic pump is applied. This arrangement with a sample taking apparatus using a peristaltic pump has, compared to the state of the art, a number of advantages. Thus, there are no technical limitations regarding sucking distance and suction height, this being because of the higher and continuous transport volumes of the peristaltic pump.

Additionally, higher suction velocities of the sample liquid are possible, since peristaltic pumps permit, as a rule, higher transport velocities and the reciprocation, such as in the case of a linear motor, is absent. Furthermore, a high dosing accuracy can be achieved, since the relatively inexact peristaltic pump is only used for transporting the liquid volume, while the metering occurs exactly, precisely and reproducibly by means of a combination of a piston pump and light barriers. Thus, the combination with a piston pump further increases the dosing accuracy. In this arrangement, the peristaltic pump is used for fast, however, less exact premetering. A fine metering of the sample liquid occurs with the downstream, piston pump.

In a special embodiment, the sample taking apparatus is embodied as a peristaltic pump, which is provided at least for coarse metering of the liquid sample into a metering container. Thus, the peristaltic pump is provided at least for coarse metering of the liquid sample into the metering container and the piston pump, respectively a syringe pump, is provided for fine metering of the liquid sample into the metering container and for transporting the metered liquid samples in the metering container into the digestion container.

In a supplementing embodiment, the transport and dosing system includes at least one pump and a metering container connected with the pump, wherein the liquid containers are connected with the digestion container via the metering container.

In a further embodiment, at least a first light barrier is provided on the metering container, which ascertains and monitors the finest predetermined dosed volume of the liquid samples in the metering container as a limit-level. Furthermore, a number of light barriers can be provided on the metering container for limit level determination of different metering volumes. At least a second light barrier is provided on the metering container, which is provided as a safety limit level switch or ascertains and monitors a greater predetermined dosed volume of the liquid samples in the metering container.

The measuring transducer in an additional embodiment is embodied of at least one photometric sensor having at least one light source for irradiating the digestion container along a measuring path with measuring light and with at least one light receiver for registering the intensity of the measuring light emitted by the light source after having passed through the measuring path. The measuring transducer can have a photometric sensor with a light source for irradiating the digestion container along a measuring path with measuring light and a light receiver for registering the intensity of the measuring light emitted by the light source after having passed through the measuring path, wherein the measuring path enters into the digestion container in a region of the outer wall of the digestion container not covered by the heater and leaves the digestion container in a region of the outer wall of the digestion container not covered by the heater.

In a supplementing embodiment, a number of liquid containers are provided, which contain the reagents to be added to the liquid sample, a standard solution and/or rinsing/washing liquid, and which are connected with the digestion container, wherein the transport and dosing system is embodied to withdraw from the liquid containers, in each case, a predetermined liquid amount and to transport such into the digestion container.

In an additional embodiment, the liquid containers are connected with the metering container via liquid transport lines each controllable by at least one valve, wherein the transport and dosing system has a central valve control mechanism, which is embodied to actuate at least a portion of the valves, especially all valves. The liquid containers can be connected with the metering container via liquid transport lines each of which is controllable by at least one valve, wherein the transport and dosing system has a central valve control mechanism, which is embodied to actuate at least a portion of the valves, especially all valves. The central control mechanism associated with one or more valves can be embodied, for example, as described in German patent application DE 102011075762 A1.

In a special embodiment, an evaluation and control system is provided, which is embodied, especially by controlling the supply, and dosing, system, to guide the liquid sample and/or predetermined amounts of the liquids from the liquid containers into the digestion container and/or which is embodied, based on a measurement signal of the measuring transducer, to ascertain the parameter of the liquid sample. The analytical device can further comprise an evaluation and control system, which is embodied, especially by controlling the supply, and dosing, system, to guide the liquid sample and/or the predetermined amounts of the liquids from the liquid containers into the digestion container and/or which is embodied, based on a measurement signal of the measuring transducer, to determine and monitor the fill level of the liquid sample in the digestion container. The evaluation and control system can comprise a data processing system, which includes at least one processor and a program memory, in which is stored a computer program, which can be executed by the processor and which serves for control of the analytical device and evaluation of the measurement signals produced by means of the measuring transducer for determining a value of the digestion parameter. For interaction with the analytical device, the evaluation and control system can include input means, e.g. a keyboard or one or more switches, and a display.

BRIEF DESCRIPTION OF THE DRAWINGS

The invention will now be explained in greater detail based on the example of an embodiment illustrated in the appended drawing, the figures of which show as follows.

DETAILED DISCUSSION IN CONJUNCTION WITH THE DRAWINGS

Figure 1:
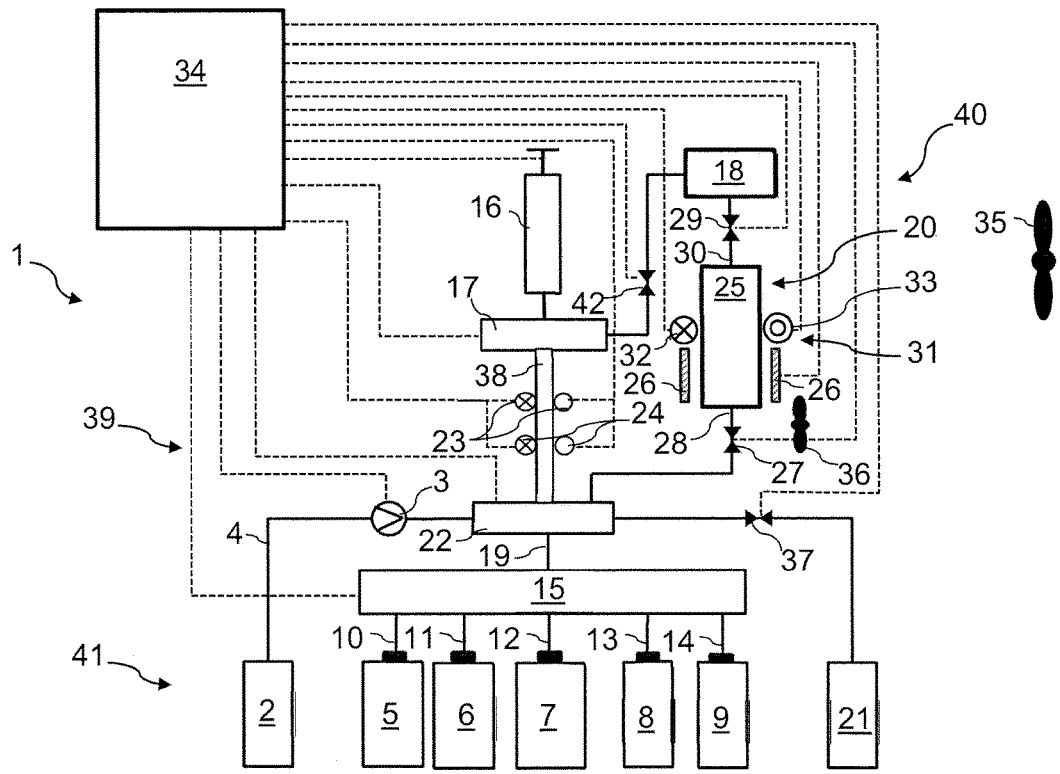
FIG. 1 is a schematic representation of an analytical device for determining the chemical oxygen demand of a liquid sample.

The analytical device 1 schematically shown in FIG. 1 serves for determining the chemical oxygen demand of a liquid sample of a monitored liquid present at a sample taking location 2. Although the example described here and in the following relates to an embodiment of an analytical device for determining the chemical oxygen demand, the invention is nevertheless equally applicable to analytical devices for directly determining the most varied of digestion parameters, for example, total carbon or total nitrogen.

The analytical device 1 is composed essentially of a container system 41 (which includes at least one sample taking location 2 and at least liquid containers 5, 6, 7, 8, 9), a reactor system 40 composed of at least one digestion reactor 20, a heating apparatus 26, a measuring transducer 31, and the transport and dosing system 39 of the invention composed of at least one peristaltic pump 3, at least one piston pump 16 and at least one metering container 38.

The sample taking location 2 can be, for example, an open vat or flume or a closed container, for example, a pipeline. The liquid can be, for example, waste water to be treated in a clarification plant. Serving for removal of the liquid sample from the sample taking location 2 in the example shown here is a sample taking apparatus 3, which can comprise, for example, a pump. The liquid transport line 4 is connected with a metering container 38.

The analytical device 1 includes a number of liquid containers 5, 6, 7, 8 and 9 of a container system 41, which contain the reagents to be added to the liquid sample for determining the COD, and standard solutions for calibrating and/or adjusting the analytical device 1. In the example shown here, a first liquid container 5 contains an aqueous potassium dichromate solution as digestion agent, a second liquid container 6 contains an aqueous mercury sulfate solution for masking chloride ions contained, in given cases, in the liquid and a third liquid container 7 contains sulfuric acid. A fourth liquid container 8 contains a first standard solution, which has a first predetermined chemical oxygen demand. A fifth liquid container 9 contains a second standard solution with a second chemical oxygen demand different from the first chemical oxygen demand. In the present example, the second standard solution is deionized water to provide a zero standard.

The liquid containers 5, 6, 7, 8, 9 are connected via liquid transport lines 10, 11, 12, 13, 14 with a liquid transport line 19 opening into the metering container 38. The liquid transport lines 10, 11, 12, 13 and 14 are each controlled by valve, wherein a here only schematically indicated, central valve control mechanism 15 serves for actuation of valves contained in the mechanism. Metering container 38 is connected with a piston pump 16, which is actuatable by means of a linear motor (not shown in FIG. 1). Arranged between the piston pump and the metering container 38 is an upper support 17 of the metering container 38, which connects the piston pump 16, the metering container 38 and the atmosphere (via a fourth valve 42) selectively with one another. Provided in this upper support 17 can be a three-way valve, which controls the supply of air from the atmosphere 18 into the metering container 38 or into the piston pump 16 and the pumping of the piston pump 17 into, respectively from, the metering container. Metering container 38 is, moreover, connected with a digestion reactor 20, which serves simultaneously for the digestion of a liquid sample and as measuring cell for determining the chemical oxygen demand.

Arranged between the metering container 38, the liquid transport line 4, the liquid transport line 19, the digestion reactor 20 and a waste container 21 is a lower support 22, which connects the metering container 38 selectively via the liquid transport line 4 and the pump 3 with the sample taking location 2 and via the liquid transport line 19 with the liquid transport lines 10, 11, 12, 13, 14 leading to the liquid containers 5,6,7,8, 9, with the digestion reactor 20 and with the waste container 21 via the third valve 37. Metering container 38 includes two light barriers 23, 24, which serve for determining the fill level of a liquid in the metering container 38. Provided in this lower support 22 can also be a multi-valve arrangement, which enables control of the inflow and outflow of the different fluids, respectively into the metering container 38 and the digestion reactor 25.

The digestion reactor 20 comprises, formed of a transparent material, e.g. glass, a digestion container 25, which is heatable by a heating apparatus 26. Opening into the digestion container 25 is a liquid transport line 28 connectable by means of a first valve 27 selectively with the metering container 38 or with the waste container 21. Moreover, digestion container 25 includes, controlled by a second valve 29, a pressure equalizing line 30, by means of which the digestion container 25 is connectable with the atmosphere 18. Digestion container 25 is embodied as standing hollow cylinder of glass having a cylinder axis Z. The axis is not shown in FIG. 1. Liquid transport line 28 opens into the lower region of the hollow cylinder, especially into its base, in order to enable an as complete as possible emptying of the digestion container 25. Pressure equalizing line 30 opens into an oppositely lying, upper region of the hollow cylinder. The outer wall 39 of the digestion container includes besides the base surfaces, which contain the line ends and which lie opposite one another, a cylindrical, lateral surface extending concentrically with the cylinder axis Z.

The sample taking apparatus 3, the metering container 38, the piston pump 16, the central valve control mechanism 15, the multi-path valve arrangement 22, the valves actuatable by the central valve control mechanism, as well as the valves 27, 29 form a transport and dosing system of the analytical device 1, which serves for the transport and dosing of the liquid sample, as well as reagents to be added to the liquid sample, into the digestion reactor 20.

The analytical device 1 includes for ascertaining a measured value representing the chemical oxygen demand of the liquid sample a photometric sensor 31, which has a light source 32 and a light receiver 33. The light source 32 can comprise, for example, one or more LEDs, especially LEDs emitting light of different wavelengths, or one or more multi-color LEDs, while the light receiver 33 can have one or more photodiodes. Measuring light emitted by the light source 32 irradiates the digestion container 25 along a measuring path extending through the reaction mixture contained in the digestion container 25 and then strikes the light receiver 33.

The photometric sensor 31 produces, as a function of the intensity of the light striking the light receiver 33, an electrical measurement signal, which, in given cases, is amplified and/or digitized by a sensor circuit (not shown). The light intensity striking on the light receiver 33 depends on the extinction, respectively absorption, of the reaction mixture contained in the digestion container 25. The light source 32 in the present example is embodied in such a manner that it emits, as a measuring light, light of least one wavelength, whose absorption or extinction is a measure for the consumption of the digestion means serving for oxidation of oxidizable components of the liquid sample. In the present example, the digestion means is potassium dichromate. Thus, the electrical measurement signal produced by the photometric sensor 31 is a measure for the chemical oxygen demand of the liquid sample.

The analytical device 1 includes, finally, an evaluation and control system 34. This includes an electronic data processing system, which has one or more processors and one or more data and program memories. The evaluation and control system 34 is connected with the photometric sensor 31 and obtains from such the measurement signal, which is, in given cases, digitized and amplified. Stored in a memory of the evaluation and control system 34 is a computer program executable by the one or more processors and serving for ascertaining the chemical oxygen demand based on the measurement signal representing an extinction or absorption by the reaction mixture.

The evaluation and control system 34 is, moreover, connected with the individual components of the transport and dosing system of the analytical device 1, especially the pumps, the central valve control mechanism 15 and the individual valves 17, 22, 27, 28, in order to control transport of predetermined liquid amounts from the sample taking location and predetermined reagent amounts from the liquid containers 5, 6 and 7 into the digestion container 25 for performing a determining of the chemical oxygen demand. Equally, the evaluation and control system 34 can control the performing of calibration measurements by withdrawing by means of the transport and dosing system, instead of from the sample taking location 2, from one or both of the standard-liquid containers 8, 9 a predetermined amount of a standard solution as liquid sample. The evaluation and control system 34 can be embodied, based on such a calibration measurement, to conduct an adjusting of the analytical device 1. Moreover, the evaluation and control system 34 can be connected with the heating apparatus 26, in order to control the heating of a reaction mixture contained in the digestion container 25.

The heating apparatus 26 includes, for example, two mutually opposing, identically embodied, heating surfaces, which have concave heating surfaces applied against the outer wall of the digestion container 25. The total surface area of the heating surfaces is less than the surface area of the cylindrical, lateral surface of the outer wall. The thereby remaining, free regions of the outer wall can provide the measuring path of the photometric sensor 31.

The analytical device can have a housing (not shown in FIG. 1) enclosing the liquid containers, the dosing, metering and supply system, the pressure reactor and the evaluation and control system. Arranged within the housing can be one or more housing ventilators 35. An additional, reactor ventilator 36 can be located in the direct vicinity of the digestion reactor 20.

The process flow for photometrically determining the chemical oxygen demand of a liquid sample by means of the analytical device 1 is, for example, as follows:

First, by means of the sample taking apparatus 3, especially a peristaltic pump 3, liquid is transported via the liquid transport line 4 and via the lower support 22 of the metering container 38 from the sample taking location 2 into the metering container 38. In such case, the liquid transport lines 10, 11, 12, 13, 14 leading to the liquid containers 5, 6, 7, 8, 9, 21 and the digestion reactor 20 are closed by valves of the central valve control mechanism 15. The fourth valve 42 is, in such case, so set that the metering container 38 is connected via the liquid transport line and the upper support 17 of the metering container 38 with the atmosphere 18. If the fill level in the metering container 38 reaches the lower light barrier 24, transport of liquid into the metering container 38 is ended. There can also be a number of such light barriers 23, 24 provided at different heights on the metering container 38, whereby differently sized metered units can be measured. Furthermore, a second light barrier 23 can be applied as a safety light barrier, in order that no reagents or sample liquid can reach the piston pump 16. As soon as the liquid level in the metering container 38 reaches the second light barrier as safety light barrier, the pumps 3, 16 are immediately stopped and, in given cases, the metered quantity in the metering container 38 disposed of into the waste container 21 by opening the third valve 37. By means of the piston pump 16, a terminal, fine metering of the sample taking from the sample taking location 2 in the metering container 38 accomplished by means of the peristaltic pump 3 can be performed. Thereafter, possibly the fourth valve 42 is opened to the atmosphere 18 and some air drawn into the piston pump 16. By means of this air, the piston pump 16, in the case of reclosed fourth valve 42, presses the metered amount of the sample located in the metering container 38 into the digestion container 25, in that the first valve 27 is opened for opening the liquid transport line 28 into the digestion container 25. In this way, the piston pump 16 can move the liquid contained in the metering container 38 into the digestion container 25. Then, still controlled via the central valve mechanism 15, corresponding reagents can be dosed by the piston pump 16 from the liquid containers 5, 6, 7, via the lines 10, 11, 12, into the metering container 38 and via the earlier described pump procedure be pumped by means of the piston pump 16, supplementally to the liquid sample from the sample taking location 2, into the digestion container 38. These reagents are necessary for digesting the sample liquid for analysis of the liquid sample.

Alternatively to the liquid sample removed from the sample taking location 2, for the case, in which a calibrating and/or adjusting is to be performed, in analogous manner, also a predetermined amount of the two standard solutions or a mixture of the two standard solutions can be transported from the containers 8, 9 into the digestion container 25. The further handling of the calibration measurement is identical to the following described additional steps of the COD determination.

To the liquid sample provided in the digestion container is added, respectively, a predetermined amount of sulfuric acid, mercury sulfate serving as masking means, as well as potassium dichromate serving as digestion agent. These reagents are dosed by means of the piston pump 16 with the cooperation of the central valve switching mechanism 15, the valve 27 controlling the liquid transport line 28 of the digestion reactor 20, the atmosphere valve 42 and the pressure equalizing valve 29 and transported into the digestion container 25. Serving for metering, in analogous manner as earlier described for the sample metering, are the light barriers 23, 24.

Then, the liquid transport line 28 and the pressure equalizing line 30 opening into the digestion container 25 are closed by means of the valves 27 and 29 and the heating apparatus 26 turned on. The heating apparatus 26 heats the reaction mixture comprising the liquid sample and the added reagents located in the digestion container 25 to a temperature of about 175° C. at a pressure of 5 to 10 bar and holds this temperature constant. Upon the beginning of the heating procedure, virtually continuously, the extinction and/or absorption of the reaction mixture is determined by means of the photometric sensor 31. The extinction, respectively absorption, values are evaluated by means of the evaluating and control system 34. Advantageously, the heating apparatus 26 is embodied as heating surfaces, which are placed on the container wall of the digestion container 25.

As soon as a specified state is reached with reference to the extinction or absorption, the extinction or absorption measuring is ended. The specified state can be a minimum rate of change of the extinction or absorption, for example, a change of the extinction of less than one percent in 10 seconds. The measured value of the extinction or absorption present upon reaching the specified state is used by the control and evaluating system for determining the chemical oxygen demand of the sample. After reaching the specified state, the digestion of the liquid sample can be ended and the heating apparatus 26 turned off. For disposal of consumed reaction mixture from the digestion container 25 via the liquid transport line 28 and the lower support 22 of the metering container 38, reaction mixture is pumped by the piston pump 16 first into the metering container 38 and, thereafter, by opening the third valve 37, transported into the waste container 21. For faster emptying, the metered amount can be predetermined by the upper light barrier 23, which serves also as safety light barrier for protection against contamination of the piston pump 16 by reagents or sample liquid, whereby a faster emptying is enabled. Also a plurality of such light barriers can be placed at different heights on the metering container 38, whereby various small metering units can be measured and pumped.

In an alternative method, the digestion of the liquid sample can be performed by heating the reaction mixture under pressure for a predetermined time, e.g. at 175° C. and a pressure of 5 to 10 bar for a time period of 30 to 120 minutes. A virtually continuous monitoring of the extinction, respectively absorption, is, in this case, not required. It can be performed, however, for example, for obtaining additional information. After expiration of the predetermined period of time, the extinction and/or absorption of the reaction mixture can be registered and used for determining the COD value of the liquid sample. The used reaction mixture can, such as above described, be cooled off and fed to the waste container 21.

All method steps described here are performed automatically by the control and evaluating system 34 in the example described here. By means of an output and input unit (not shown), the operator can display the measured values or visualize the method steps on a display and input parameters into the control and evaluating system 34.

Figure 2:
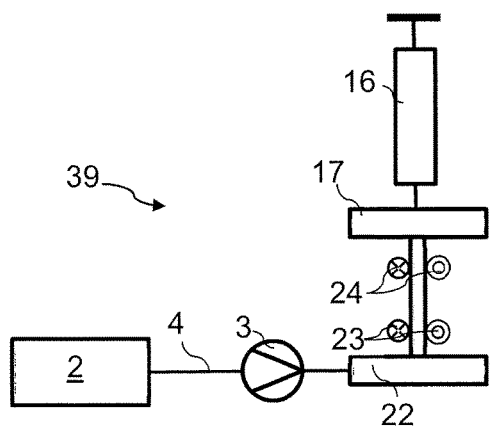
FIG. 2 is a schematic representation of the metering system of the analytical device illustrated in FIG. 1.

FIG. 2 shows just the supply and metering system 39 of the invention from FIG. 1. As already described for FIG. 1, a peristaltic pump 3 is used for sample taking from the sample taking location 2. By means of this arrangement, the sucking distance and sucking height can be improved due to the greater and continuous transport volume of the peristaltic pump 3 compared to the piston pump 16 for the sample taking from the farther removed sample taking container 2. Furthermore, higher metering rates and more exact dosing accuracy of the sample liquid are achieved with this combination of peristaltic pump 3 and piston pump 16. In this arrangement, the peristaltic pump 3 is used for fast, however, less exact, premetering, respectively coarse metering. Fine metering occurs by means of the piston pump 16, in that a lacking amount of the sample liquid is pulled into, or an excess amount pressed out of, the metering container 38. The operation and construction of this supply and metering system 39 of the invention have already been sufficiently treated in the description of FIG. 1.

LIST OF REFERENCE CHARACTERS 1. analytical device
2. sample taking location, sample container
3. sample taking apparatus, peristaltic pump
4. sample liquid transport line
5. first liquid container
6. second liquid container
7. third liquid container
8. fourth liquid container
9. fifth liquid container
10. first liquid transport line
11. second liquid transport line
12. third liquid transport line
13. fourth liquid transport line
14. fifth liquid transport line
15. central valve control mechanism
16. piston pump, syringe pump
17. upper support
18. atmosphere, air
19. reagents transporting line
20. digestion reactor
21. waste container
22. lower support
23. first light barrier
24. second light barrier
25. digestion container, pressure reactor
26. heating apparatus
27. first valve
28. sixth liquid transport line
29. second valve
30. pressure equalizing line
31. measuring transducer, photometric sensor
32. light source
33. light receiver, photodiode
34. evaluation and control system
35. housing ventilator
36. reactor ventilator
37. third valve
38. metering container
39. transport and dosing system
40. reactor system
41. container system
42. fourth valve

The invention claimed is:

1. An analytical device for determining a parameter of a liquid sample, including a digestion parameter, such as chemical oxygen demand, total carbon content or total nitrogen content, comprising:
    a reactor system including a digestion chamber for ascertaining the parameter of a liquid sample and a measuring transducer disposed on opposing sides of the digestion chamber along a measuring path that extends through the digestion chamber, the measuring transducer configured to register a measured parameter correlated with a measured value of the liquid sample mixed with one or more reagents in the digestion chamber;
    a container system including a plurality of containers for storing samples, reagents and waste products; and
    a transport and dosing system for metering and transporting the liquid sample and reagents from said containers into a metering container and for disposal of waste products from said metering container into a waste container, wherein the metering container includes a plurality of light barriers adjacent said metering container and configured for limit level determination of different metering volumes within the metering container,
    wherein:
        said transport and dosing system includes the metering container, a piston pump and a sample taking apparatus comprising a peristaltic pump at least for removal from a sample taking location of a predetermined volume of a liquid as the liquid sample;
        the sample taking location is connected with said metering container by a liquid transport line;
        the peristaltic pump is disposed between the sample taking location and the metering container and is embodied to transport the liquid sample from said sample taking location through said liquid transport line into said metering container; and
        the metering container is further connected with the digestion chamber via the piston pump.

2. The analytical device as claimed in claim 1, wherein said peristaltic pump provides at least coarse metering of the liquid sample into said metering container.

3. The analytical device as claimed in claim 1, wherein said piston pump transports liquid samples metered into said metering container into the digestion chamber.

4. The analytical device as claimed in claim 1, wherein said liquid containers are connected with the digestion chamber via said metering container.

5. The analytical device as claimed in claim 1, wherein at least one of the plurality of light barriers is provided as a safety limit level switch for said metering container.

6. The analytical device as claimed in claim 1, wherein said measuring transducer includes at least one photometric sensor with at least one light source for irradiating the digestion chamber along the measuring path with measuring light and with at least one light receiver for registering intensity of the measuring light emitted by said light source after having traversed the measuring path.

7. The analytical device as a claimed in claim 4, wherein:
certain of said liquid containers contain reagents to be added to the liquid sample, a standard solution, and/or rinsing/washing liquid; and
said transport and dosing system is embodied to withdraw from said liquid containers, in each case, a predetermined liquid amount and to transport such into the digestion chamber.

8. The analytical device as claimed in claim 7, wherein:
said liquid containers are connected with said metering container via liquid transport lines each controllable by at least one valve; and
said transport and dosing system includes a central valve control mechanism, which is embodied to actuate all valves.

9. The analytical device as a claimed in claim 1, further comprising:
an evaluation and control system including at least one processor and at least data and program memories, the evaluation and control system embodied to control the transport and dosing system to guide the liquid sample and/or predetermined amounts of the liquids from said liquid containers into the digestion chamber, and/or the evaluation and control system embodied, based on a measurement signal of said measuring transducer, to ascertain the parameter of the liquid sample.

10. The analytical device as claimed in claim 3, wherein said piston pump provides fine metering of the liquid sample into the metering container.

11. The analytical device as claimed in claim 1, further comprising an upper support of the metering container disposed between the piston pump and the metering container, the upper support comprising a three-way valve configured to selectively connect the metering container with either the piston pump or an atmosphere outside the metering container.

12. The analytical device as claimed in claim 1, the analytical device further comprising a means of a combination of the piston pump and the light barrier for a high dosing accuracy.

* * * * *